United States Patent [19]

Milkowski et al.

[11] 4,064,128
[45] * Dec. 20, 1977

[54] N,[3-(4'-FLUOROBENZOYL)PROPYL]-N$_2$-(2'-CHLORO-5'-METHYLPHENOXY)ETHYL]-PIPERAZINE

[75] Inventors: Wolfgang Milkowski, Burgdorf; Horst Zeugner, Hannover; Klaus-Wolf von Eickstedt, Berlin; Werner Stühmer, Eldagsen, all of Germany

[73] Assignee: Kali-Chemie Aktiengesellschaft, Hannover, Germany

[*] Notice: The portion of the term of this patent subsequent to July 13, 1993, has been disclaimed.

[21] Appl. No.: 683,336

[22] Filed: May 5, 1976

Related U.S. Application Data

[63] Continuation-in-part of Ser. No. 589,121, June 20, 1975, Pat. No. 3,969,356, which is a continuation-in-part of Ser. No. 288,320, Sept. 12, 1972, abandoned.

[30] Foreign Application Priority Data

Sept. 13, 1971 Germany .............................. 2145682

[51] Int. Cl.$^2$ ............................................ C07D 295/10
[52] U.S. Cl. ........................ 260/268 R; 260/239 BC; 424/244; 424/250
[58] Field of Search ..................................... 260/268 R

*Primary Examiner*—Donald G. Daus
*Assistant Examiner*—David B. Springer
*Attorney, Agent, or Firm*—Michael J. Striker

[57] ABSTRACT

N$_1$-[3-(4'-fluorobenzoyl)-propyl]-N$_2$-[2-(2'-chloro-5'-methylphenoxy)ethyl]-piperazine of the formula

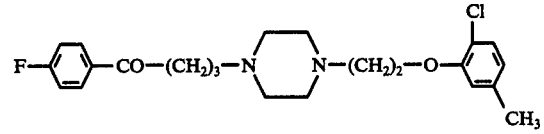

or a pharmaceutically acceptable salt thereof. The compounds are sedatives of low toxicity.

2 Claims, No Drawings

N,[3-(4'-FLUOROBENZOYL)PROPYL]-N₂-(2'-CHLORO-5'-METHYLPHENOXY)ETHYL]PIPERAZINE

CROSS-REFERENCE TO RELATED APPLICATIONS

This application is a continuation-in-part of application Ser. No. 589,121 filed by the same inventors on June 20, 1975, now U.S. Pat. No. 3,969,356 issued July 13, 1976 which in turn was a continuation of application Ser. No. 288,320 filed by the same inventors on Sept. 12, 1972 now abandoned. The two parent applications were filed in respect of 1,4-diazacycloalkane derivatives, salts thereof and method of making.

BACKGROUND OF THE INVENTION

Compounds have already been proposed as sedatives which have the following general formula

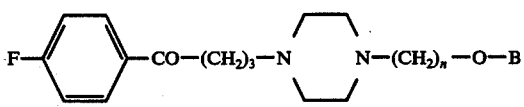

in which B is 4-chlorophenyl (German published application 20 27 051).

Other compounds of this general type are described in U.S. Pat. No. 3,637,704 to Umemoto as having the following formula:

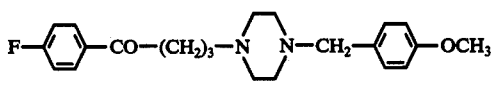

In a variant of this compound described in the same patent, the methoxy group is replaced by a 4-fluorobenzyl group.

Other piperazines of the fluorobenzoylpropyl substituted type have been disclosed in the above identified parent application, Ser. No. 589,121. Among these compounds was the compound of the present application.

DISCUSSION OF THE INVENTION

The compound of the invention first disclosed in application Ser. No. 589,121 is obtained as follows:

6.1 g of N-[2-(2'-chloro-5'-methylphenoxy)-ethyl]-piperazine, 6.4 g of 4-(p-fluorophenyl)-4,4-ethylendioxy-1-chlorbutane, 5 g of potassium carbonate and 2.9 g of potassium bromide were heated to boiling point under reflux in 100 ml methylisobutylketone for 36 hours. The hot solution was then filtered. After cooling down the filtrate was stirred with 10% hydrochloric acid. The dihydrochloride thereby precipitated as a white crystalline precipitate. The salt was removed by filtration and recrystallized from ethanol/water. The yield was 7 g. The melting point of the compound was between 227° and 230° C.

On the basis of comparative tests it has been found that this compound of the invention is distinguished by an unusual therapeutic breadth in that it combines low toxicity with a high sedative effect. Of the compounds tested for comparison purposes are some disclosed in the above parent application 589,121. Among these is the compound where B is 4-nitrophenyl and specifically which is the dihydrochloride hydrate of this compound.

The nitrophenyl compound has the formula:

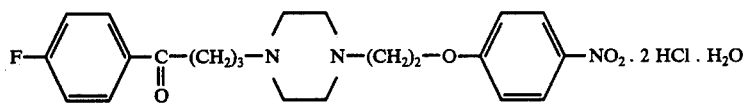

It may be obtained as follows:

39.2 g of N-[2-(4'-nitrophenoxy)-ethyl]-piperazine and 31.2 g of 4-fluoro-γ-chlorobutyrophenone were heated on an oil bath for 6 hours to 120° to 130° C. The reaction mass was cooled to 70° C and was then taken up in a small amount of benzene and filtered over 500 g of aluminum oxide (III) according to the Brockmann method. After evaporation of the solvent there were obtained 40 g of crude base. The base was dissolved in ethanol and converted with HCl gas to the dihydrochloride. The salt was separated by filtration and recrystallized from ethanol with 20% water. There was thus obtained the dihydrochloride hydrate at a yield of 28.3 g. The melting point was between 223° and 225° C.

An alternative process of making the compound is also disclosed in Ser. No. 589,121.

Other compounds tested and disclosed in the parent application are the following, all having the formula

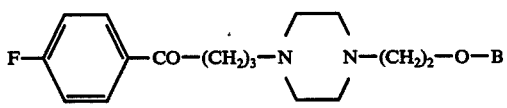

wherein B is as follows:

4-chloro-2-methylphenyl: (Example 28 of 589,121)
2,3-dimethylphenyl: (Example 34 of the parent)
2,5-dimethylphenyl: (Example 35 of the parent)
3,5-dimethylphenyl: (Example 36 of the parent).

These compounds are made by the same process as the compound of the invention employing corresponding starting compounds.

In addition, comparative tests were also carried out with the compound wherein B is 2,6-dichlorophenyl, melting point 212° to 221° C and the compounds of the art disclosed in German application 20 27 059 and U.S. Pat. No. 3,637,704 to Umemoto identified above in the background section of the present specification. In these latter compounds B is 4-chlorophenyl or B is 4-methoxy- or 4-fluorobenzyl which latter two groups, however, are directly attached to the N₂-atom of the piperazine-ring.

The procedure followed in the tests regarding properties of the compound of the invention and comparative compounds was as follows:

Test 1. Acute oral toxicity

The acute oral toxicity (LD₅₀p.o.) was determined by peroral administration of a single dose of the compound to fasting white male mice.

The lethal dose in terms of milligrams of the compound per kilogram of body weight of the tested animals was computed in accordance with the method described by J. P. Litchfeld and F. Wilcoxon in Journal of Pharmacology and Experimental Therapeutics, vol. 96, page 99 (1949).

The doses that are referred to herein were all computed in accordance with the said method. The results in this test were based upon a survival period of 7 days.

Test 2. Sleep prolongation test

In this test a dose of the test compound is first administered perorally to female mice. After an interval of 30 minutes a dose of 65 milligrams of hexobarbital per kilogram of body weight of the animal is administered intravenously to the mice. The length of the period after administration of the hexabarbital during which the mouse remains sleeping on its side before turning over onto its abdomen, is then noted. The result is reported as milligrams of the test compound per kilogram of body weight of the mouse that is required to prolong by a factor of 4 the duration of the period of sleep that is produced when only the specified dose of hexobarbital is administered.

Test 3. Inhibition of aggression induced by clonidine

This test was described by C. Morpurgo in European Journal of Pharmacology, vol. 3, pages 374–377 (1968), for measuring the effectiveness of compounds in inhibiting combat or aggression behaviour produced by administration of clonidine. In this test 12 mice are separated into pairs and each mouse is injected intraperitoneally with a dose of the test compound. After an interval of 30 minutes a dose equivalent to 46.4 milligrams of clonidine per kilogram of body weight is administered intraperitoneally to each mouse. Clonidine at this dosage level produces an aggressive behaviour in the mice which expresses itself in violent bouts of fighting and biting. The mice are observed and their behaviour scored in accordance with a point system. The mice are observed during a period of 30 minutes and each pair of mice scores 2 points if, during any 10 minute interval, two or more encounters or bouts had occurred. Six pairs of mice accordingly cannot score more than a total of 36 points during the 30 minute period, which is rated 100%. From these results the effective dose ($ED_{50}$) of the test compound in milligrams per kilogram of body weight of the mouse is computed in accordance with the method described by Litchfield and Wilcoxon in the publication that was referred to hereinbefore in connection with Test 1.

Test 4. Analgesic effect

The analgesic effect of the substance was determined by the Writhing test. The substances to be tested were administered to male albino mice (NMRI strain) in accordance with the method described by E. Sigmund, R. Cadmus and G. Lu in Proc. Soc. exp. Biol., N.Y. 95 (1957), page 729. After 30 minutes, 1.5 mg. of phenyl quinone per kg. of body weight were administered to the test animals through the abdominal cavity. Amidopyrine was orally administered as comparison substance in a dose of 100 mg/kg. The figures set out in Table 2 indicate the oral doses of the compounds according to the invention in mg/kg which produce the same effect as the dose of the comparison substance.

Test 5. Antihistamine action

The antihistamine action was determined following the Magnus procedure and using an ileum portion of a length of 2 cm obtained from Pirbright guinea pigs (Pharmakologische Methoden, Leopold Ther, Wissenschaftliche Verlagsanstalt Stuttgart, 1949). The $ED_{50}$ has been given in mol/1.

The results of the tests described appear from the following Table.

TABLE

| Group B equals: | $LD_{50}$ p.o. mg/kg | Fourfold prolongation of hexobarbital sleep duration mg/kg | Aggression test (Morpurgo) mg/kg | Writhing-test mg/kg | Antihistamine action $ED_{50}$ mol/l |
|---|---|---|---|---|---|
| 2-chloro-5-methylphenyl (invention) | 464 | 7 | 0.35 | 6 | $7 \times 10^{-9}$ |
| | | Comparative tests | | | |
| 4-nitrophenyl | 215 | 8 | 0.7 | 1.8 | $4 \times 10^{-9}$ |
| 4-chloro-2-methylphenyl | 1000 | 100 | 2.5 | 68.1 | $1.7 \times 10^{-8}$ |
| 2,6-dichlorophenyl | 1016 | 117 | 7.4 | n.r. | n.r. |
| 2,3-dimethylphenyl | 1038 | 120 | 4.6 | 23.0 | n.r. |
| 2,5-dimethylphenyl | 1235 | 100 | n.r. | 17.0 | n.r. |
| 3,5-dimethylphenyl | 297 | 68 | n.r. | 6.9 | n.r. |
| 4-chlorophenyl (German appl.20 27 054) | 336 | 21.5 | 6.0 | 5.5 | $9 \times 10^{-9}$ |
| methoxyphenyl, no O-bridge (U.S. 3,637,704 Umemoto) | 431 | 33.9 | 4.7 | 62.0 | $1.5 \times 10^{-7}$ |
| fluorobenzyl, no O-bridge (Umemoto) | 431 | 18.5 | 7.6 | 49.5 | $1.2 \times 10^{-7}$ | n.r. = not reported (not tested).

Surprisingly, it is found from the above tests that the compound of the invention is distinguished by a low toxicity in combination with a high sedative effect. Its toxicity is very substantially lower than that of 4-nitrophenyl while its sedative effect, as evidenced by the prolongation of the sleep duration after hexobarbital and by the aggression test is the same or better than that of the 4-nitrophenyl compound.

Four of the chloromethyl or dichloro or dimethylphenyl compounds have substantially lower toxicity values. However, their sedative action is poor as compared with the compound of the invention when measured by the prolongation of sleep duration and the aggression test.

The 3,5-dimethylphenyl has even a higher toxicity and likewise a less satisfactory sedative effect.

The compounds of the prior art either have a greater toxicity or about the same toxicity, but all have considerably lower sedative effects. The analgesic action of the Umemoto compounds also is substantially lower than that of the compound of the invention.

Of particular interest is the comparison of the 2-chloro-5-methylphenyl compound of the invention with the 4-chloro-2-methylphenyl compound which was disclosed in the parent application. In this case we have the same types of substituents, but in different positions. From the substantially better results in regard to sedative effects, it appears that the position of the substituents in the phenyl ring of group B is critical.

The compound of the invention therefore appears to exhibit a fortunate combination of low toxicity and high sedative and good analgesic effects.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. $N_1$-[3-(4'-fluorobenzoyl)-propyl]-$N_2$-(2'-chloro-5'-methylphenoxy)ethyl]-piperazine of the formula

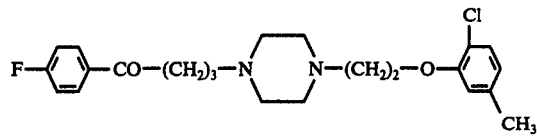

or a pharmaceutically acceptable salt thereof.

2. The compound of claim 1 which is the dihydrochloride salt thereof.

* * * * *